United States Patent [19]

Sugiyama et al.

[11] Patent Number: 5,136,053
[45] Date of Patent: Aug. 4, 1992

[54] METHOD FOR PRODUCING A CYCLIC ALKYLENEIMINE

[75] Inventors: Hitoshi Sugiyama; Tomoyuki Mori, both of Kurashiki, Japan

[73] Assignee: Mitsubishi Kasei Corporation, Tokyo, Japan

[21] Appl. No.: 487,401

[22] Filed: Mar. 2, 1990

[30] Foreign Application Priority Data

Mar. 20, 1989 [JP] Japan .................... 1-69037

[51] Int. Cl.$^5$ .................. C07D 207/06; C07D 207/12; C07D 203.04; C07D 211/00
[52] U.S. Cl. .................................... 548/579; 548/541; 548/543; 548/954; 548/968; 548/959; 548/960; 548/950; 548/952; 546/184; 546/242; 546/243; 540/526; 540/604; 540/612; 540/482; 540/450
[58] Field of Search ............... 548/579, 541, 543, 954, 548/968, 959, 960, 950, 952; 546/184, 242, 243; 540/526, 604, 612, 482, 450

[56] References Cited

U.S. PATENT DOCUMENTS

| | | | |
|---|---|---|---|
| 2,525,584 | 10/1950 | Bordner | 548/400 |
| 2,600,289 | 6/1952 | Bordner | 548/400 |
| 3,086,017 | 4/1963 | Denton | 544/106 |
| 3,635,952 | 1/1972 | Tyssee | 546/184 |
| 3,853,887 | 12/1974 | Pinke et al. | 548/400 |

FOREIGN PATENT DOCUMENTS

| | | | |
|---|---|---|---|
| 18-19940 | 8/1943 | Japan | 548/579 |
| 19940 | 8/1968 | Japan | 548/579 |
| 268681 | 10/1989 | Japan | 548/579 |
| 467069 | 4/1973 | U.S.S.R. | 548/579 |

OTHER PUBLICATIONS

Ono et al.; Journal of Catalysis; 41; pp. 322-328 (1976).
Fujita et al.; Journal of Catalysis, 35 (pp. 325-329) (1974).
Zhurnal obshchei Khimii vol. VIII, No. 13, pp. 1868-1873 (1937).
Journal of the Japan Petroleum Institute, vol. 20, No. 5, 419 (1977).
J. Catalysis 41, 322-328 (1976).

*Primary Examiner*—Mary C. Lee
*Assistant Examiner*—Robert C. Whittenbaugh
*Attorney, Agent, or Firm*—Oblon, Spivak, McClelland, Maier & Neustadt

[57] ABSTRACT

A method for producing a cyclic alkyleneimine, which comprises reacting a cyclic ether with a compound of the formula $NH_2R$ wherein R is a hydrogen atom or an alkyl group, in a vapor phase in the presence of a solid acid catalyst, wherein the reaction is conducted under a pressure of at least 0.5 kg/cm$^2$ G as the total pressure of partial pressures of the reactants and the reaction product.

18 Claims, No Drawings

METHOD FOR PRODUCING A CYCLIC ALKYLENEIMINE

The present invention relates to a method for producing a cyclic alkyleneimine.

Heretofore, the following various methods have been proposed for the production of pyrrolidine by reacting tetrahydrofuran with ammonia in a vapor phase in the presence of a catalyst.

1) A method in which tetrahydrofuran and ammonia are reacted at 400° C. in the presence of an alumina catalyst to obtain pyrrolidine (Chemical Abstracts, Vol. 32, 548 (1938)).

2) A method wherein tetrahydrofuran and ammonia are reacted at a temperature of from 275° to 375° C. in the presence of a γ-alumina catalyst using ammonia in an exess amount ($NH_3/THF = 6$-$20$ mols/1 mol) and by recycling high boiling point by-products, to obtain pyrrolidine (U.S. Pat. No. 2,525,584;.

3) A method wherein tetrahydrofuran and ammonia are reacted using a γ-alumina catalyst treated with boric acid, to obtain pyrrolidine (Japanese Examined Patent Publication No. 19940/1968).

4) A method wherein tetrahydrofuran and ammonia are reacted in the presence of a zeolite catalyst to obtain pyrrolidine (Journal of Catalysis, 35, 325–329 (1974)).

However, in the above methods 1) and 2), the conversion of tetrahydrofuran and the selectivity to pyrrolidine are low. In the above method 3), the selectivity is improved over the methods 1) and 2), but the conversion of tetrahydrofuran is inadequate. If the conversion is increased by raising the reaction temperature, the selectivity tends to deteriorate. It is therefore impossible to obtain the reaction results satisfactory in both the conversion and the selectivity. In the method 4), the conversion of tetrahydrofuran is inadequate, and the method is not satisfactory from the industrial point of view.

In view of the above problems of the conventional techniques, the present inventors have conducted extensive researches on a method for producing cyclic alkyleneimines in an industrially advantageous manner. As a result, they have found it possible to remarkably improve the reaction activities and the selectivity by reacting a cyclic ether with a compound of the formula $NH_2R$ wherein R is a hydrogen atom or an alkyl group, under a certain specific pressure by means of a solid acid catalyst and thereby to obtain a method which is fully satisfactory from the industrial point of view. The present invention has been accomplished on the basis of this discovery.

The present invention provides a method for producing a cyclic alkyleneimine, which comprises reacting a cyclic ether with a compound of the formula $NH_2R$ wherein R is a hydrogen atom or an alkyl group, in a vapor phase in the presence of a solid acid catalyst, wherein the reaction is conducted under a pressure of at least 0.5 kg/cm²G as the total pressure of partial pressures of the reactants and the reaction product.

Now, the present invention will be described in detail with reference to the preferred embodiments.

There is no particular restriction as to the cyclic ether to be used as the starting material in the method of the present invention. Usually, however, a compound of the formula:

wherein $R_1$ is a $C_2$-$C_{12}$ polymethylene group which is unsubstituted or substituted by an alkyl group, an alkylene group, an aryl group or an alkoxy group, or a $C_2$-$C_{10}$ polymethylene heterochain group containing in the chain one or two hetero atoms selected from the group consisting of nitrogen, oxygen and sulfur, is used. More specifically, propylene oxide, tetramethylene oxide (i.e. tetrahydrofuran), pentamethylene oxide (i.e. tetrahydropyran), cyclohexene oxide, styrene oxide, dioxane and morpholine may be mentioned.

As the other starting material, a compound of the formula $NH_2R$ wherein R is a hydrogen atom or an alkyl group, is used. Specifically, ammonia or a primary amine may be mentioned. As the primary amine, a lower alkylamine having from 1 to 4 carbon atoms such as methylamine, ethylamine, propylamine or butylamine, is usually employed.

The solid acid catalyst to be used in the present invention, includes, for example, zeolite, alumina, silica-alumina, silica-magnesium oxide and silica-zirconium oxide. Particularly preferred are zeolite, alumina and silica-alumina. As the zeolite, faujasite type zeolite and chabazite type zeolite having at least a part of cation sites is ion-exchanged with hydrogen, ammonium or polyvalent metal cations. As the faujasite type zeolite, X-type zeolite and Y-type zeolite may be mentioned. As the chabazite type zeolite, L-type zeolite may be mentioned.

The faujasite type zeolite or L-type zeolite is usually available in the form which contains an ion-exchangeable alkali metal such as sodium or potassium, irrespective of the natural product or the synthetic product. The faujasite-type zeolite or L-type zeolite wherein such cation sites are alkali metals such as sodium or potassium, is poor in the catalytic activities by itself. Therefore, it is usually possible to improve the catalytic activities by ion-exchanging at least a part, preferably at least 20%, more preferably at least 40%, most preferably at least 50%, of the alkali metal ions such as sodium or potassium at the cation sites by hydrogen ions, ammonium ions or polyvalent (usually bivalent or trivalent) metal ions.

As the cations for ion-exchange, one or more cations are selected from the group consisting of hydrogen ions, ammonium ions and polyvalent metal ions (preferably bivalent and trivalent metal ions). The bivalent and trivalent metal ions include cations of magnesium, calcium, strontium, barium, zinc, cadmium, lead, manganese, tin, cobalt, nickel, iron, cerium, lanthanum.

The above mentioned ion exchange can be conducted by various known methods. For example, the above mentioned faujasite-type zeolite is immersed in an aqueous solution of a salt (a chloride, a nitrate, a sulfate or an organic acid salt) of the above mentioned cation for ion-exchange until a predetermined ion-exchange rate is attained, followed by solid-liquid separation. The ion exchanged zeolite as the separated solid component is thoroughly washed with water and dried.

In the method of the present invention, the above mentioned cyclic ether and the compound of the formula $NH_2R$ wherein R is a hydrogen atom or an alkyl group, are catalytically reacted in a vapor phase in the presence of the above mentioned solid acid catalyst under a pressure of at least 0.5 kg/cm² G as the total pressure of partial pressures of the reactants and the reaction product.

The above reaction is conducted usually at a reaction temperature within a range of from 250° to 400° C., preferably from 300° to 380° C. under a reaction pressure of at least 0.5 kg/cm² G, preferably from 0.5 to 50 kg/cm² G, more preferably from 1 to 20 kg/cm² G, most preferably from 2 to 15 kg/cm² G, as the total pressure of partial pressures of the reactants and the reaction product. If the reaction temperature is too low, the reaction rate decreases, and if it is too high, side reactions increase, such being undesirable. If the reaction pressure is lower than the lower limit, the activities (the reaction rate) and the selectivity remarkably deteriorate. The molar ratio of the compound of the formula NH₂R to the cyclic ether is usually within a range of from 1 to 50, preferably from 2 to 30, more preferably from 5 to 20. To carry out the method of the present invention, the reaction is conducted usually in the form of a common vapor phase catalytic reaction. It can be conducted either in a fixed bed system or a fluidized bed system. The space velocity (the total gas amount of the cyclic ether and the compound of the formula NH₂R under a standard condition (1/hr)/catalyst(l)) may be varied within a wide range depending upon such conditions as the reaction temperature and the molar ratio of the compound of the formula NH₂R to the cyclic ether. However, usually a space velocity within a range of from 50 to 4,000 hr⁻¹, preferably from 100 to 3,000 hr⁻¹, is employed. If the space velocity is too small, side-reactions increase, and if it is too large, the amount of unreacted materials to be recovered increases, such being undesirable.

Cyclic alkyleneimines obtained by the above reaction are useful as intermediates for the preparation of e.g., pharmaceutical, insecticides or rubber accelerators.

The present invention can be used particularly advantageously for the production of pyrrolidine or an N-alkylpyrrolidine from tetrahydrofuran and the compound of the formula NH₂R.

Now, the present invention will be described in further detail with reference to Examples. However, it should be understood that the present invention is by no means restricted by such specific Examples.

The zeolite catalysts used in the following Examples and Comparative Examples were prepared or pretreated, respectively, by the following methods.

(A) Catalyst 1:H-X zeolite

Na-X zeolite (Molecular Sieve Type 13X: Na$_{86}$[(AlO$_2$)$_{86}$(SiO$_2$)$_{106}$]xH$_2$O, manufactured by Union Showa K.K.) was ion-exchanged to NH$_4$-X zeolite, and then subjected to baking pretreatment to obtain H-X zeolite.

Namely, into an aqueous solution obtained by dissolving 51.5 g of NH$_4$Cl in 300 ml of water, 30 g of the above Na-X zeolite was introduced and ion-exchanged at 70° C. for two hours. This ion-exchange operation was repeated three times. Then, the zeolite was washed with deionized water at room temperature, collected by filtration and then dried at 100° C. for 12 hours to obtain NH$_4$-X zeolite. This zeolite was molded into particles having a diameter of from 1 to 2 mm, then baked at 400° C. for one hour in air and further at 400° C. for one hour in nitrogen, to obtain H-X zeolite.

(B) Catalyst 2:H-L zeolite

K-L zeolite (Molecular Sieve SK-45, manufactured by Union Showa K.K.) was ion-exchanged to obtain NH$_4$-L zeolite, followed by baking pretreatment to obtain H-L zeolite.

(C) Catalyst 3:alumina

Commercially available alumina catalyst (SCM-250, manufactured by Rhone-Poulenc S.A.) was molded into particles having a diameter of from 1 to 2 mm. Then, it was pretreated by baking at 400° C. for one hour in air and further at 400° C. for one hour in nitrogen.

(D) Catalyst 4:silica-alumina

Commercially available silica-alumina catalyst (N-631HN, manufactured by Nikki K.K.) was molded into particles having a diameter of from 1 to 2 mm. Then, it was pretreated by baking at 400° C. for one hour in air and further at 400° C. for one hour in nitrogen.

EXAMPLES 1 TO 13

90 cc of glass beads were packed in an upper portion of a SUS-316 reaction tube (inner diameter: 25 mm, length: 480 mm) as a preheating zone for evaporation of the cyclic ether and ammonia, and a catalyst of the type and amount as identified in Table 1 was packed therebelow as a reaction zone. The preheating zone for evaporation and the reaction zone of the reaction tube were heated, respectively, by ring-shaped electric furnaces from outside and controlled to maintain such zones at predetermined temperatures.

Then, tetrahydrofuran (THF) and ammonia were supplied to the reaction zone in the amounts as identified in Table 1 and controlled to the ratio as identified in Table 1 and reacted under the reaction conditions as identified in Table 1, whereby the obtained reaction product was condensed and collected in a trap cooled with an ethylene glycol-water cooling medium. The liquid reaction product thus obtained was analyzed by gas chromatography. The non-condensed gas component was collected in a gas state and analyzed by gas chromatography. The results are shown in Table 1.

COMPARATIVE EXAMPLES 1 TO 4

The same operation as in Examples 1 to 10 was conducted except that the reaction pressure was changed to atmospheric pressure. The results are shown in Table 1.

TABLE 1

|  | Examples | | | | | | | | |
|---|---|---|---|---|---|---|---|---|---|
|  | 1 | 2 | 3 | 4 | 5 | 6 | 7 | 8 | 9 |
| Type of catalyst | Cat. 1 | Cat. 1 | Cat. 1 | Cat. 2 | Cat. 2 | Cat. 3 | Cat. 3 | Cat. 4 | Cat. 4 |
| Amount of catalyst (g) | 20 | 20 | 20 | 20 | 20 | 20 | 20 | 20 | 20 |
| Amounts of feed materials |  |  |  |  |  |  |  |  |  |
| THF (mmol/hr) | 294 | 294 | 294 | 294 | 295 | 296 | 296 | 294 | 295 |
| NH$_3$ (mmol/hr) | 2080 | 2080 | 2080 | 2080 | 2080 | 2080 | 2080 | 2080 | 2080 |
| NH$_3$/THF (molar ratio) | 7 | 7 | 7 | 7 | 7 | 7 | 7 | 7 | 7 |

TABLE 1-continued

| Reaction conditions | | | | | | | | | |
|---|---|---|---|---|---|---|---|---|---|
| Reaction pressure *1 ($kg/cm^2$G) | 2 | 4 | 6 | 2 | 6 | 2 | 4 | 1 | 2 |
| Reaction temp. (°C.) | 350 | 350 | 350 | 350 | 350 | 350 | 350 | 350 | 350 |
| W/F *2 (g · hr/mol) | 8.4 | 8.4 | 8.4 | 8.4 | 8.4 | 8.4 | 8.4 | 8.4 | 8.4 |
| Space velocity ($hr^{-1}$) | 1600 | 1600 | 1600 | 1600 | 1600 | 1600 | 1600 | 1600 | 1600 |
| Results | | | | | | | | | |
| THF conversion (%) | 66.7 | 68.8 | 70.1 | 47.9 | 54.8 | 81.8 | 87.3 | 69.0 | 77.4 |
| Selectivity for pyrrolidine (%) | 91.8 | 91.9 | 93.1 | 92.5 | 91.3 | 66.2 | 63.0 | 79.8 | 85.0 |

| | Examples | | | | Comparative Examples | | | |
|---|---|---|---|---|---|---|---|---|
| | 10 | 11 | 12 | 13 | 1 | 2 | 3 | 4 |
| Type of catalyst | Cat. 4 | Cat. 4 | Cat. 4 | Cat. 4 | Cat. 1 | Cat. 2 | Cat. 3 | Cat. 4 |
| Amount of catalyst (g) | 20 | 20 | 20 | 20 | 20 | 20 | 20 | 20 |
| Amounts of feed materials | | | | | | | | |
| THF (mmol/hr) | 294 | 299 | 110 | 114 | 293 | 294 | 297 | 297 |
| $NH_3$ (mmol/hr) | 2080 | 2080 | 2268 | 2268 | 2080 | 2080 | 2080 | 2080 |
| $NH_3$/THF (molar ratio) | 7 | 7 | 20 | 20 | 7 | 7 | 7 | 7 |
| Reaction conditions | | | | | | | | |
| Reaction pressure *1 ($kg/cm^2$G) | 6 | 10 | 2 | 10 | 0 | 0 | 0 | 0 |
| Reaction temp. (°C.) | 350 | 350 | 350 | 350 | 350 | 350 | 350 | 350 |
| W/F *2 (g · hr/mol) | 8.4 | 8.4 | 8.4 | 8.4 | 8.4 | 8.4 | 8.4 | 8.4 |
| Space velocity ($hr^{-1}$) | 1600 | 1600 | 1600 | 1600 | 1600 | 1600 | 1600 | 1600 |
| Results | | | | | | | | |
| THF conversion (%) | 88.7 | 92.4 | 96.8 | 99.2 | 50.4 | 24.8 | 72.6 | 51.4 |
| Selectivity for pyrrolidine (%) | 90.2 | 93.2 | 91.8 | 96.7 | 90.3 | 73.5 | 56.7 | 72.7 |

*1 Reaction pressure: Total pressure of partial pressures of the reactants and the reaction product.
*2 W: Amount of catalyst (g), F: Total amounts of feed materials (mol/hr)

According to the method of the present invention, it is possible to produce a cyclic alkyleneimine at a high conversion and at a high selectivity from a cyclic ether and ammonia or a primary amine.

We claim:

1. A method for producing a cyclic alkyleneimine, which comprises reacting a cyclic ether with a compound of the formula $NH_2R$ wherein R is a hydrogen atom or an alkyl group, in a vapor phase in the presence of a solid acid catalyst, wherein the reaction is conducted under a pressure of at least 0.5 kg/cm² G as the total pressure of partial pressures of the reactions and the reaction product and wherein said cyclic ether is a compound of the formula:

wherein $R_1$ is a $C_2$-$C_{12}$ polymethylene group which is unsubstituted or substituted by an alkyl group, an alkylene group, an aryl group or an alkoxy group.

2. The method of claim 1, wherein said reaction is conducted under a pressure of at least 1 kg/cm² G.

3. The method according to claim 1, wherein the cyclic ether is a compound of the formula:

wherein $R_1$ is a $C_2$-$C_{12}$ polymethylene group which is unsubstituted or substituted by an alkyl group, an alkylene group, an aryl group or an alkoxy group.

4. The method according to claim 1, wherein the cyclic ether is selected from the group consisting of propylene oxide, tetrahydrofuran and tetrahydropyran.

5. The method according to claim 4, wherein the cyclic ether is tetrahydrofuran.

6. The method according to claim 1, wherein the compound of the formula $NH_2R$ is a lower alkylamine having from 1 to 4 carbon atoms.

7. The method according to claim 1, wherein the compound of the formula $NH_2R$ is ammonia.

8. The method according to claim 1, wherein the solid acid catalyst is selected from the group consisting of zeolite, alumina, silica-alumina, silica magnesium oxide and silica-zirconium oxide.

9. The method according to claim 8, wherein the solid acid catalyst is selected from the group consisting of zeolite, silica-alumina and alumina.

10. The method according to claim 8, wherein the solid acid catalyst is silica-alumina.

11. The method according to claim 1, wherein the reaction temperature is within a range of from 250° to 400° C.

12. The method according to claim 1, wherein the reaction temperature is within a range of from 300° to 380° C.

13. The method according to claim 1, wherein the reaction pressure is within a range of from 0.5 to 50 kg/cm² G as the total pressure of partial pressures of the reactants and the reaction product.

14. The method according to claim 13, wherein the reaction pressure is within a range of from 1 to 20 kg/cm² G as the total pressure of partial pressures of the reactants and the reaction products.

15. The method according to claim 13, wherein the reaction pressure is within a range of from 2 to 15 kg/cm² G as the total pressure of partial pressures of the reactants and reaction product.

16. The method according to claim 1, wherein the molar ratio of the compound of the formula NH$_2$R to the cyclic ether in the reaction system is within a range of from 1 to 50.

17. The method according to claim 16, wherein the molar ratio of the compound of the formula NH2R to the cyclic ether is within a range of from 2 to 30.

18. The method according to claim 16, wherein the molar ratio of the compound of the formula NH$_2$R to the cyclic ether is within a range of from 5 to 20.

* * * * *